United States Patent [19]

Duffett

[11] Patent Number: Plant 5,996

[45] Date of Patent: May 19, 1987

[54] CHRYSANTHEMUM PLANT NAMED FALMA

[75] Inventor: William E. Duffett, Salinas, Calif.

[73] Assignee: Yoder Brothers, Inc., Barberton, Ohio

[21] Appl. No.: 776,967

[22] Filed: Sep. 17, 1985

[51] Int. Cl.[4] ..... A01H 5/00

[52] U.S. Cl. ..... Plt./79

[58] Field of Search ..... Plt./79

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Falma having flat capitulum form; decorative capitulum type; yellow orange ray floret color; diameter across face of capitulum ranging from 5 to 6.5 cm. at maturity; uniform nine week photoperiodic flowering response to short days; tall plant height when grown single stem; 15 to 25 cm. peduncles on open, normally terminal sprays; and 13° C. minimum temperature tolerance for initiation and development of flowering buds.

3 Drawing Figures

The present invention comprises a new and distinct cultivar of *Chrysanthemum morifolium,* Ramat., named Falma.

Falma is a product of a planned breeding program which had the objective of creating new Chrysanthemum cultivars having low temperature tolerance for cut spray mum programs with decorative capitulum type, orange ray floret color, eight to nine week flowering response, and the ability to produce commercially acceptable quality in year-round programs. Such traits in combination were not present or required improvements in previously available commercial cultivars.

Falma, identified as 81795030, was originated from a cross made by William E. Duffett in a controlled breeding program in Salinas, Calif. in 1980. The female parent was the cultivar identified as Riot, disclosed in my U.S. Plant Pat. No. 5,403, Riot being originated from a hybridization of unnamed seedlings. The male parent of Falma, identified as 79378001, was an unnamed seedling.

Falma was discovered and selected as one flowering plant within the progeny of the stated cross by William E. Duffett on Nov. 6, 1981 in a controlled environment in Bogota, Colombia.

The first act of asexual reproduction of Falma was accomplished when vegetative cuttings were taken from the initial selection in January of 1982 in a controlled environment in Bogota, Colombia by technicians working under formulations established and supervised by William E. Duffett. Horticultural examination of selected units initiated Sept. 21, 1982 has demonstrated that the combination of characteristics as herein disclosed for Falma are firmly fixed and are retained through successive generations of asexual reproduction.

Falma has not been observed under all possible environmental conditions. The phenotype may vary significantly with variations in environment such as temperature, light intensity and day length. The observations, measurements and comparisons describe plants grown in Salinas, Calif. and Bogota, Colombia under greenhouse conditions which approximate those generally used in commercial practice.

The following traits have been repeatedly observed and are determined to be basic characteristics of Falma which in combination distinguish this chrysanthemum as a new and distinct cultivar:

(1) Flat capitulum form.

(2) Decorative capitulum type.

(3) Yellow orange ray floret color.

(4) Diameter across face of capitulum ranging from 5 to 6.5 cm. at maturity.

(5) Uniform nine week photoperiodic flowering response to short days.

(6) Medium peduncle length, ranging from 15 to 25 cm.

(7) Tall plant height, requiring two long day weeks prior to short days to attain a flowered plant height of 110 to 120 cm. for year-round flowerings.

(8) Low temperature tolerance of 13° C. for initiation and development when grown in single stem cut spray programs with a continuous dark period of 12 to 13 hours.

The accompanying photographic drawings show typical inflorescence and leaf characteristics of Falma with the colors being as nearly true as possible with illustrations of this type.

Sheet 1 is a color photograph of Falma grown as a single stem cut spray.

Sheet 2 is a black and white photograph of three views of the inflorescence of Falma.

Sheet 3 is a black and white photograph showing the upper and under sides of the leaves of Falma at three stages of development (mature, intermediate and immature).

Of the many commercial cultivars known to the present inventor the most similar in comparison to Falma is Show Off. Reference is made to attached Chart A which compares certain characteristics of Falma to those same characteristics of Show Off. Similar traits are type, form, color, response and low temperature tolerance. Falma develops longer peduncles, has a smaller capitulum diameter and a taller plant height.

In the following description, color references are made to the Munsell Book of Color, Cabinet edition, and to The Royal Horticultural Society Colour Chart.

The exact colors for corolla of ray florets are not represented in either the Munsell Book of Color (MBC) or The Royal Horticultural Society Colour Chart (RHS), and the color values given are those closest to the actual color of Falma. The color values were determined on plant material grown in Salinas, Calif. on July 18, 1985.

Classification:

*Botanical.*—*Chrysanthemum morifolium,* Ramat., cv Falma.

*Commercial.*—Decorative cut spray mum.

I. INFLORESCENCE

A. Capitulum:

*Form.*—Flat.

*Type.*—Decorative.

*Diameter across face.*—5 to 6.5 cm.

B. Corolla of ray florets:

*Color (general tonality from a distance of three meters).*—Yellow orange.

*Color (upper surface).*—MBC: 7.5 YR 6/14; RHS 22A.

*Color (under surface).*—MBC: 1.25 Y 8/12; RHS 15B.

*Shape.*—Short, broad, rounded tip.

C. Corolla of disc florets:

*Color (mature).*—RHS: 3A.

*Color (immature).*—RHS: 154A.

D. Reproductive organs:

*Androecium.*—Present disc florets only; 1–3 disc florets per inflorescence; scant pollen.

*Gynoecium.*—Present both ray and disc florets.

II. PLANT

A. General appearance:

*Height.*—Tall; 110 to 120 cm., as a flowering plant from a rooted cutting, with 14 long days for year-round flowerings maintaining a minimum nightly 12 hour continuous dark period.

B. Foliage:

*Color (upper surface).*—RHS 147A.

*Color (under surface).*—RHS 137B.

*Shape.*—Shallow lobed and moderate serration.

CHART A

COMPARISON OF FALMA AND SHOW OFF

| | RAY FLORET COLOR | CAPITULUM FORM AND TYPE | SPRAY FORMATION | DIAMETER ACROSS FACE OF CAPITULUM |
|---|---|---|---|---|
| FALMA | YELLOW ORANGE | FLAT DECORATIVE | 15 to 25 cm. PEDUNCLES | 5 to 6.5 cm. |
| SHOW OFF | AMBER BRONZE | FLAT DECORATIVE | 8 to 12 cm. PEDUNCLES | 6 to 8 cm. |

| | PLANT HEIGHT | FLOWERING RESPONSE PERIOD | LOW TEMPERATURE TOLERANCE |
|---|---|---|---|
| FALMA | TALL 110 to 120 cm. | NINE WEEKS | 13° C. |
| SHOW OFF | MEDIUM 80 to 90 cm. | NINE WEEKS | 13° C. |

COMPARISONS MADE OF PLANTS GROWN AS SINGLE STEM CUT SPARY MUMS WITH 14 LONG DAYS IN BOGOTA, COLOMBIA

I claim:

1. A new and distinct cultivar of *Chrysanthemum morifolium,* Ramat., named Falma, as described and illustrated, and particularly characterized as to uniqueness by the combined characteristics of flat capitulum form; decorative capitulum type; yellow orange ray floret color; diameter across face of capitulum ranging from 5 to 6.5 cm. at maturity; uniform nine week flowering response; tall plant height when grown single stem; 15 to 25 cm. peduncles on open, normally terminal sprays; and 13° C. minimum temperature tolerance for initiation and development of flowering buds.

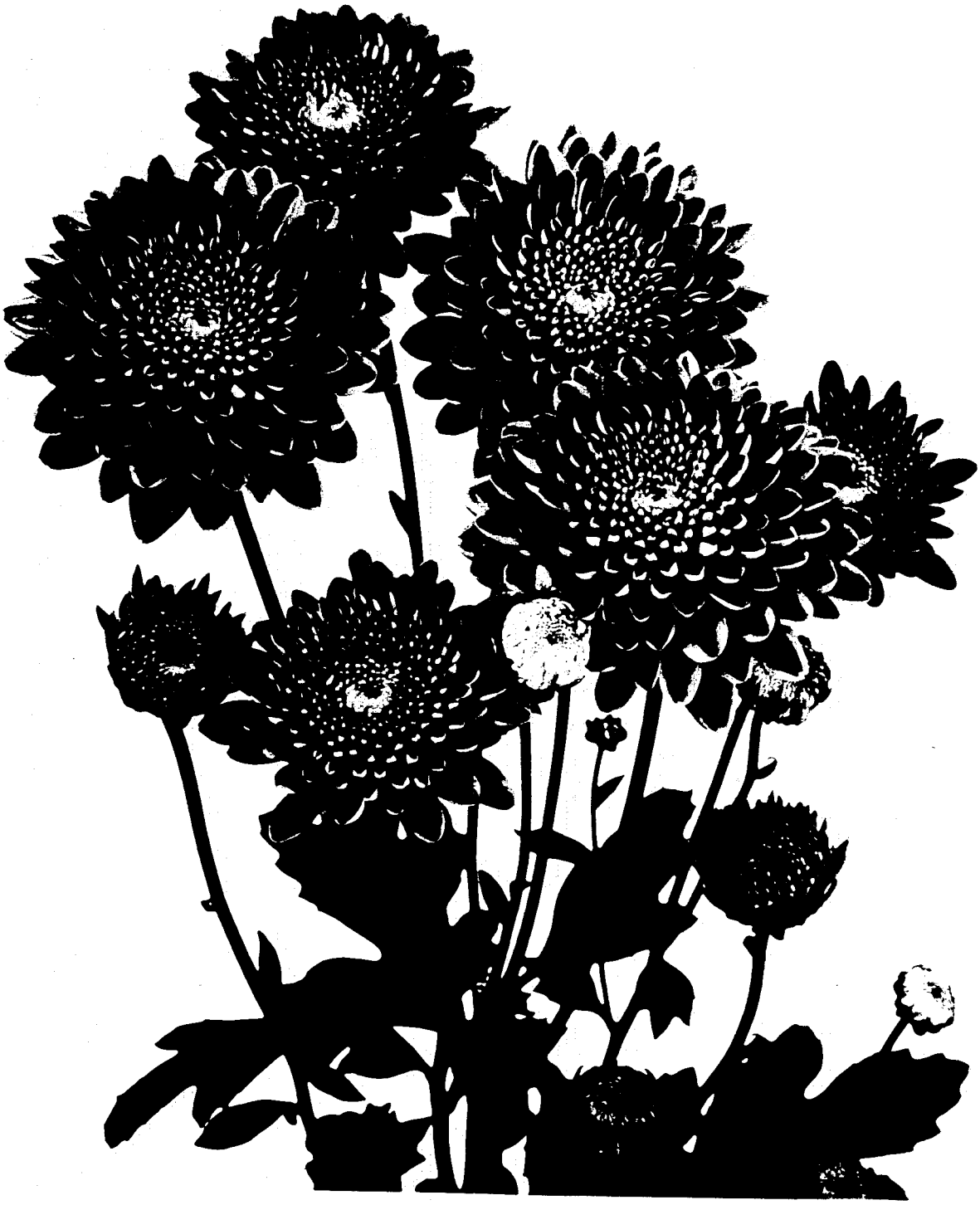

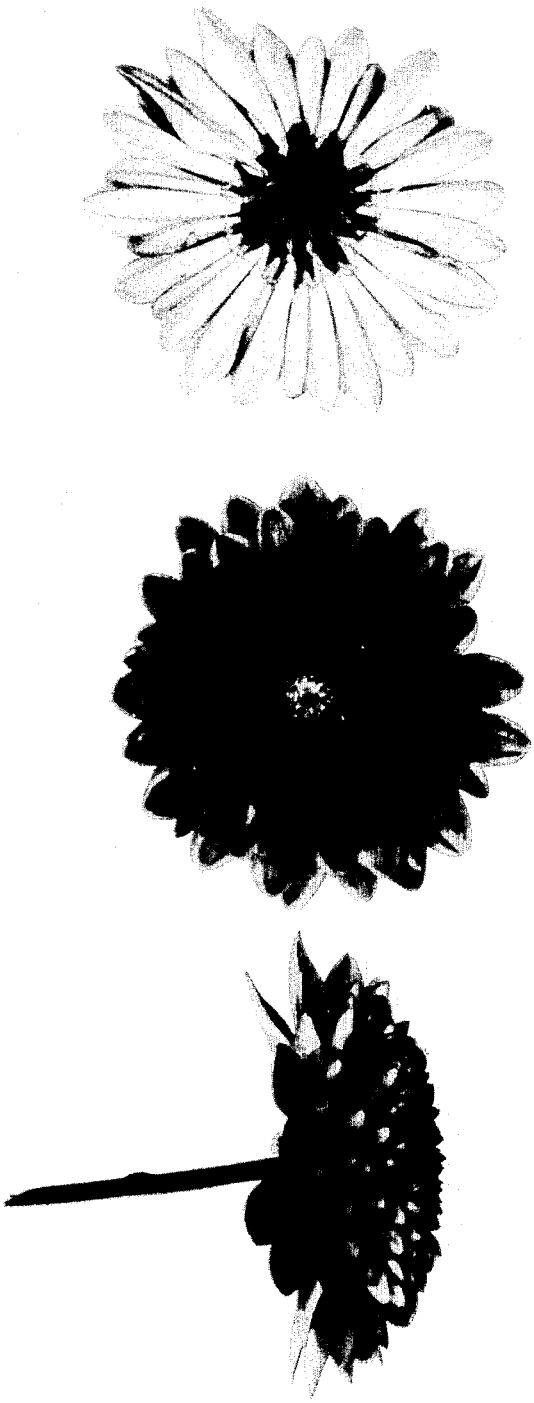

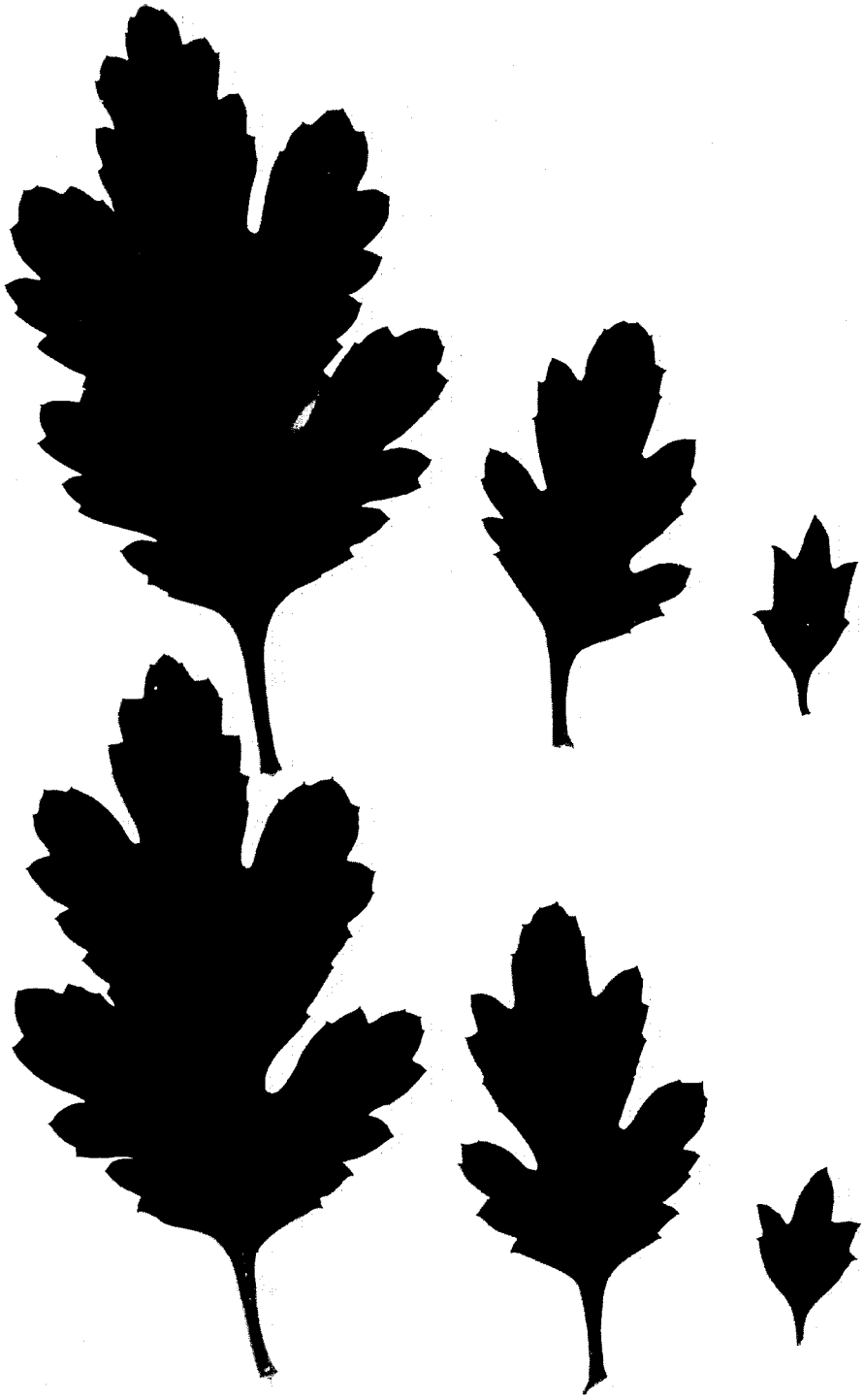

* * * * *